United States Patent

Zenner et al.

[11] Patent Number: 6,066,652
[45] Date of Patent: May 23, 2000

[54] METHOD FOR TREATING DISEASES OF THE INNER EAR USING ADAMANTANE DERIVATIVES

[75] Inventors: Hans Peter Zenner; J. Peter Ruppersberg, both of Tuebingen; Andreas Busch, Kelkheim, all of Germany

[73] Assignee: Tinnitus Forschungs-und Entwicklungs GmbH, Munich, Germany

[21] Appl. No.: 09/011,085

[22] PCT Filed: Jul. 31, 1996

[86] PCT No.: PCT/EP96/03360

§ 371 Date: Jun. 12, 1998

§ 102(e) Date: Jun. 12, 1998

[87] PCT Pub. No.: WO97/04762

PCT Pub. Date: Feb. 13, 1997

[30] Foreign Application Priority Data

Aug. 2, 1995 [DE] Germany .......................... 195 28 388

[51] Int. Cl.$^7$ ..................... A61K 31/445; A61K 31/40; A61K 31/13
[52] U.S. Cl. ..................... 514/317; 514/422; 514/662
[58] Field of Search ..................... 514/317, 422, 514/662

[56] References Cited

U.S. PATENT DOCUMENTS

| 3,328,251 | 6/1967 | Smith ..................... 167/65 |
| 4,331,686 | 5/1982 | Djurickovic ..................... 424/325 |
| 5,061,703 | 10/1991 | Bormann et al. ..................... 514/212 |

FOREIGN PATENT DOCUMENTS

| 0 392 059 | 4/1989 | European Pat. Off. . |
| 3921 062 | 1/1991 | Germany . |
| 40 14 672 | 11/1991 | Germany . |

OTHER PUBLICATIONS

H. Spoendlin: Ohr, 1990, pp. 875–878, "Allgemeine Pathologie und Pathologische Anatomie" by Max Eder et al.
Acta Otolaryngol, Bd. 115, Nr. 2, Mar. 1995, pp. 236–240 "Receptor Pharmacological Models for Inner Ear Therapies with Emphasis on Glutamate Receptors: A Survey" by K. Ehrenberger et al.
Otorhinolaryngol, Nova Bd. 5, Nr. 3–4, Mai 1995—Aug. 1995, pp. 148–152 "Rezeptorpharmakologische Modelle fur eine siehe das ganze Dokument".

*Primary Examiner*—Zohreh Fay
*Attorney, Agent, or Firm*—Pennie & Edmonds LLP

[57] ABSTRACT

Use of adamantane derivatives of the formula

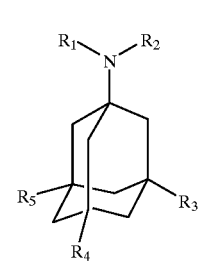

in which $R_1$ and $R_2$
are identical or different and can be hydrogen or straight-chained or branched alkyl groups having 1 to 6 carbon atoms, or
together with the nitrogen atom can represent a heterocyclic group having 5 or 6 ring atoms,
in which $R_3$ and $R_4$ are identical or different and can be hydrogen, straight-chained or branched alkyl groups having between 1 and 6 carbon atoms, cycloalkyl groups having 5 or 6 carbon atoms or a phenyl group, and in which $R_5$ is hydrogen or a straight-chained or branched alkyl group having between 1 and 6 carbon atoms for treating diseases of the inner ear.

17 Claims, No Drawings

METHOD FOR TREATING DISEASES OF THE INNER EAR USING ADAMANTANE DERIVATIVES

TECHNICAL FIELD

The invention relates to the use of adamantane derivatives of the formula

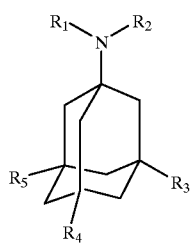

in which R1 and R2 are identical or different and can be hydrogen or straight-chained or branched alkyl groups having 1 to 6 carbon atoms, or together with the nitrogen atom can represent a heterocyclic group having 5 or 6 ring atoms, in which R3 and R4 are identical or different and can be hydrogen, straight-chained or branched alkyl groups having between 1 and 6 carbon atoms, cycloalkyl groups having 5 or 6 carbon atoms or a phenyl group, and in which R5 is hydrogen or a straight-chained or branched alkyl group having between 1 and 6 carbon atoms.

BACKGROUND OF THE INVENTION

The use of adamantane derivatives falling under the cited general formula I for the therapy of certain diseases is already known. Thus, for instance, the dopamine-related influence of amantadine (1-adamantanamine) is described in a series of publications. Also an antiviral effect of certain amino-adamantanes has been demonstrated. In addition, EP B1-392059 shows the use of adamantane derivatives in preventing and treating cerebral ischaemia. According to this publication adamantane derivatives having the formulua I as described above can protectively prevent destruction of brain cells following an ischaemia, the adamantane derivatives being employed as antagonists for the NDMA receptor channels of the nerve cells. In EP-B1-392059 both general and special methods of producing adamantane derivatives falling under the above-cited formula I are described.

The publication by Ehrenberger and Felix in Acta Otalarygnol (Stockholm) 1995; 115: 236–240 concerns neurotransmission between the inner hair cell of the inner ear and the afferent neuron. An attempt is made to explain certain illnesses of the inner ear in a model by a so-called glutamate neurotoxicity, it being indicated in this context to use antagonists which block the glutamate link of the postsynaptic membrane. It is in this context that it is also termed conceivable to use antagonists for the glycine link, the redoxmodulating location or for the NMDA receptor complex, for example an adamantane derivative. The quinoxaline derivate caroverine tested in the Ehrenberger and Felix publication fails to produce any satisfactory results in the treatment of tinnitus thought to be induced by a glutamate, however.

At the same time it is to be realized that diseases of the inner ear are widespread, especially as regards diseases or disturbances in which subjective noise in the ear, so-called tinnitus occurs. It is estimated that in Germany alone roughly 6 million people suffer from tinnitus. In roughly 800,000 cases the tinnitus is so pronounced that these patients need intensive treatment by a physician, due to the patient being seriously handicapped by tormenting ear noise. At this time no reliable therapy is available.

As regards the complexity of inner ear diseases, especially in the case of tinnitus which is still to be conclusively explained, a series of medicamentous therapies has been proposed hitherto. These include, in addition to the use of anaesthetica, for example the application of lidocaine-type antiarrhythmica or anticonvulsiva, e.g. carbamazepine. However, in most cases treatments of this kind fail to bring satisfactory results. In-patient infusion therapy with procaine appears to be the sole form of tinnitus therapy which is superior to a placebo, albeit only to a minor degree. Here too, the effect is only temporary, however.

SUMMARY OF THE INVENTION

The object of the invention is thus to define a possibility of treating diseases of the inner ear, more particularly in the case of tinnitus, with which a perceptible compensation of the symptoms associated with the disease is achieved. More particularly, the tormenting ear noise is made to disappear or diminished to such a degree that the patient reattains his normal quality of life.

This object is achieved by the use of formulua I adamantane derivatives as claimed. It has been surprisingly discovered that, more particularly, tinnitus can be effectively compensated by use of the compounds cited. Further fields of application may materialize in the treatment of chronic inner ear deafness, sudden deafness or morbus Menière. An improvement in hearing in the case of inner ear deafness can be achieved by the use in accordance with the invention.

DETAILED DESCRIPTION OF THE INVENTION

As already mentioned, the use of adamantane derivatives is possible or conceivable in many cases of diseases of the inner ear. Preferably, adamantane derivatives can be used in the case of inner ear diseases in which troublesome ear noise, so-called tinnitus occurs, especially in the case of treating such forms of tinnitus as chronic tinnitus, subacute tinnitus or also acute permanent tinnitus, since it is just these patients that require intensive therapy.

In addition to other inner ear diseases those in which tinnitus occurs often involving loss of hearing (deafness) are concerned. In a tinnitus occurrence this loss of hearing lies in the frequency range of the tinnitus, the impaired hearing being associated with a so-called positive recruitment and/or (amplitude) reduction or failure of otoacoustic emissions.

The so-called positive recruitment is a phenomenon in audiometry when a comparison of the loudness is undertaken in the case of one-sided deafness. In the case of positive recruitment a slight amplification is needed in the ear impaired in hearing to prompt the same loudness sensitivity as for the healthy ear, i.e. the loss in hearing is compensated by increasing loudness. The so-called otoacoustic emissions are noise events occurring in the external canal having to do with the condition of the middle ear or inner ear. Otoacoustic emissions may occur spontaneously, i.e. without the ear receiving external stimulation or also being evoked externally, for example with the aid of a sound emitter.

Both the occurrence of positive recruitment and the reduction or failure of otoacoustic emissions can be measured and thus an inner ear dysfunction assigned to the patients concerned.

Should a patient be inflicted simultaneously with a tinnitus and a reduction in hearing in the corresponding frequency range of the tinnitus associated with a positive recruitment and/or reduction or failure of otoacoustic emissions, it can be concluded that an impairment or dysfunction of the outer hair cells and its cochlear amplifier is involved. Since this dysfunction is improved or eliminated by the use in accordance with the invention a new active mechanism must be at the bottom of it all which is not in keeping with applications for adamantane derivatives known hitherto. It is known that, for example, no NMDA receptors exist on the outer hair cells thus eliminating any antagonistic effect for such receptors. A glutamate otoneurotoxicity as postulated by Ehrenberger/Felix does not come into question since glutamate is non-toxic for hair cells.

One possible explanation may be that the adamantane derivatives directly affect other receptors present on the outer hair cells, for example, purine receptors and acetylcholine receptors. In addition to this, there are indications as to a further mechanism which relates to the effect of adamantane derivatives with subsequent steps in stimulation transmission by which the adamantane derivatives may obstruct the cation transporter relaying the return transport of neurotransmitters from the synaptic gap in the presynapse, resulting in a depletion of the neurotransmitter in the efferent presynapsis and thus (indirectly) in reduced stimulation of receptors. This mechanism developing at the presynapse, i.e. before the synaptic gap could be effective in the form described along the full hearing passage up to the auditory cortex.

Formula I adamantane derivatives can be employed as described by the formula or preferably in the form of their pharmaceutically acceptable salts, hydrobromides, sulphates, acetates, succinates, tartrates, for example, or, more particularly, the hydrochlorides belonging to these additional salts. Likewise, other salts as usual may be represented and employed.

The quantity of the adamantane derivatives used is normally not critical, it materializing for the person skilled in the art as usual from values gained from experience or by implementing trial and error tests prior to application. Expediently the quantities used are typically between approximately 0.01 and approximately 100 mg/kg body-weight, preferably from approximately 0.1 to approximately 1 mg/kg body-weight, whereby quantities of approximately 0.1 to approximately 0.5 mg/kg body-weight are preferred in the last-mentioned range.

As mentioned, the invention covers the use of all formula I amino adamantanes for treatment of diseases of the inner ear. Examples of such compounds are listed, for example, in EP-B1-392059, the contents of which are accordingly made that of the present description.

Preferred formula I compounds are those in which R1 and R2 signify hydrogen H and compounds in which R5 and, more particularly, additionally R1 and R2 signify the hydrogen residue.

In the already cited preferred compounds and also in other formula I compounds the residues R3 and R4 are optionally a methyl or ethyl residue.

One particularly preferred compound employable in accordance with the invention is memantine, i.e. 1-amino-3.5-dimethyladamantane or the hydrochloride thereof, memantine HCl. This compound or its salt is particularly suitable for the treatment of diseases of the inner ear, especially in treating tinnitus.

The invention otherwise involves also a method of treating diseases of the inner ear in which an effective quantity of an adamantane derivative having the general formula I is administered. A corresponding method is suitable, more particularly, for the treatment of tinnitus, reference being made to the particular aspects of the administration already described as regards the compounds employable and the quantities used.

One preferred embodiment of the use in accordance with the invention materializes from the description of a clinical application example described in the following, whereby the individual features resulting therefrom may be achieved singly or in combination with each other.

EXAMPLE

In a prospective clinical case control study 104 patients were treated with a drug containing the adamantane derivative 1-amino-3.5-dimethyl adamantane (memantine).

All patients suffered from a cochlear tinnitus associated with deafness in the frequency range in which the tinnitus occurred. A positive recruitment and a significant amplitude reduction or failure of otoacoustic emissions existed as diagnosed by usual audiometric methods. The treated group of patients totalling 104 in number comprised patients having chronic tinnitus, subacute tinnitus and acute permanent tinnitus.

The medicament used was the preparation Akatinol Memantine" of the Company Merz & Co., GmbH & Co, Frankfurt am Main. The active substance of this preparation is memantine HCL along with lactose, magnesium stearate, polyaminoethacrylate, among other things, as the usual pharmaceutical media and expedients. Such pharmaceutical media and expedients may be present, of course, as usual in all embodiments of the invention so that they can be administered, for example, in the form of tablets, dragees, sterile solutions or injections.

In the clinical study the patients were administered the active substance initially by infusions. Up to the 5th day they received typically a quantity of 10 mg/d (daily), this quantity being increased to 20 mg/d as of the 6th day. Depending on the patient concerned an abrupt improvement in the complaints occurred between the 6th and 8th day in the group of those responding to treatment.

The infusion treatment was continued until the 10th day with a quantity of 20 mg/d. As of the 10th day two tablets, each containing 10 mg of the active substance memantine HCl were administered.

In some cases the dose was higher, without, however, ever exceeding a quantity of maximally 30 mg/d.

In the study long-term compensation of tinnitus was achieved in the case of approximately 72% of patients having chronic tinnitus, 82% having subacute tinnitus and in all patients having acute permanent tinnitus. Although in the majority of the cases two 10 mg tablets needed to be administered daily continually to maintain the effect a few patients remained free of symptoms even after ceasing application of the preparation.

The study already clearly shows, however, a considerable improvement as compared to known attempts of therapy indicating as a rule only a temporary relief despite permanent medication. In this context the advantages of the invention are evident directly in comparison with a control group of patients treated with the preparation Lidocaine as already mentioned. This group too, showed the inner ear dysfunction with chronic tinnitus, subacute tinnitus or acute permanent tinnitus. Thus, the proportion of patients in which a significant improvement occurred between the 6th and 10th day was significantly less in the case of lidocaine administration.

What is claimed is:

1. A method for treating tinnitus associated with at least one condition selected from the group consisting of positive recruitment and a reduction or failure of oto-acoustic emissions in a human patient by administering to said patient a therapeutically effective amount of at least one adamantane derivative having a formula:

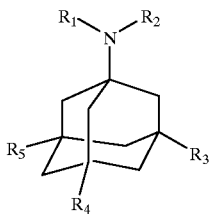

wherein $R_1$ and $R_2$ are the same or different and are selected from hydrogen or straight chain or branched alkyl groups with from 1 to 6 carbon atoms or where, together with the nitrogen atom, they form a heterocyclic group comprising 5 or 6 ring atoms, and wherein $R_3$ and $R_4$ are the same or different and are selected from hydrogen, straight-chain or branched alkyl groups with from 1 to 6 carbon atoms, cycloalkyl groups with 5 or 6 carbon atoms, or a phenyl group, and wherein $R_5$ is selected from hydrogen or a straight-chain or branched alkyl group with from 1 to 6 carbon atoms, to remedy the condition and thus treat the tinnitus.

2. The method according to claim 1 wherein the tinnitus is associated with impaired hearing.

3. The method according to claim 2 wherein the tinnitus is associated with said impaired hearing in the frequency range of the tinnitus.

4. The method according to claim 1 wherein said therapeutically effective amount is selected to range from about 0.01 to about 100 mg/kg of said patient's body weight.

5. The method according to claim 1 wherein said therapeutically effective amount is selected to range from about 0.1 to about 1 mg/kg of said patient's body weight.

6. The method according to claim 1 wherein said therapeutically effective amount is selected to range from about 0.1 to about 0.5 mg/kg of said patient's body weight.

7. The method according to claim 1 wherein $R_1$ and $R_2$ are selected to be a hydrogen atom.

8. The method according to claim 1 wherein $R_5$ is selected to be a hydrogen atom.

9. The method according to claim 1 wherein $R_1$, $R_2$ and $R_5$ are selected to be hydrogen atoms.

10. The method according to claim 1 wherein $R_3$ and $R_4$ are selected from the group consisting of methyl and ethyl groups.

11. The method according to claim 1 wherein the adamantane derivative is administered in a form selected from a salt, a hydrobromide, a sulphate, an acetate, a succinate or a tartrate.

12. The method according to claim 11 wherein the adamantane derivative is administered in the form of a hydrochloride salt.

13. The method according to claim 1 wherein the adamantane derivative is selected to be 3.5-dimethyl-1-adamantane.

14. The method according to claim 13 wherein the adamantane derivative is selected to be 3.5-dimethyl-1-adamantane hydrochloride.

15. The method according to claim 1 wherein the tinnitus is subacute or chronic tinnitus.

16. The method according to claim 1 wherein the adamantane derivative is administered in the form of a tablet, a dragee, a sterile solution or an injection.

17. A method for treating tinnitus associated with at least one condition selected from the group consisting of positive recruitment and a reduction or failure of oto-acoustic emissions in a human patient by administering to said human patient a therapeutic amount of 3,5-dimethyl-1-adamantane or its hydrochloride salt, wherein said therapeutic amount is selected to range from about 0.01 to about 100 mg/kg of said patient's body weight, to remedy the condition and thus treat the tinnitus.

* * * * *